(12) United States Patent
Henry et al.

(10) Patent No.: US 6,253,604 B1
(45) Date of Patent: Jul. 3, 2001

(54) SCANNER WITH INTERIOR GAUGING HEAD AND COMBINED DUST AND DRIVE BELT

(75) Inventors: Lee Henry, San Jose; Steven Nelson, Oroville, both of CA (US)

(73) Assignee: Impact Systems, Inc., Jamestown, CA (US)

( * ) Notice: Subject to any disclaimer, the term of this patent is extended or adjusted under 35 U.S.C. 154(b) by 0 days.

(21) Appl. No.: 09/487,058

(22) Filed: Jan. 19, 2000

(51) Int. Cl.[7] .............................. G01L 5/04; D21F 11/00; D21F 7/06; D21F 13/00
(52) U.S. Cl. .................. 73/159; 73/73; 162/198; 162/263
(58) Field of Search .................. 73/159, 160, 73; 226/45; 250/339.1, 341.1; 162/198, 263, DIG. 4, DIG. 10

(56) References Cited

U.S. PATENT DOCUMENTS

| 4,766,315 | * | 8/1988 | Hellstrom et al. | 250/339 |
|---|---|---|---|---|
| 5,298,122 | * | 3/1994 | Munch et al. | 162/259 |
| 5,928,475 | * | 7/1999 | Chase et al. | 162/198 |
| 6,080,278 | * | 6/2000 | Heaven et al. | 162/198 |

* cited by examiner

Primary Examiner—Hezron Williams
Assistant Examiner—Dennis Loo
(74) Attorney, Agent, or Firm—Coudert Brothers

(57) ABSTRACT

A scanner for moving sheet material such as a paper-making machine provides the gauging heads which measure parameters such as basis weight and moisture entirely inside an enclosed tubular beam. Each gauging head is driven by a single belt which both drives the gauging head in a cross direction perpendicular to the moving sheet direction and provides for dust and dirt protection by covering a slot in the beam, except where the gauging head is located.

8 Claims, 4 Drawing Sheets

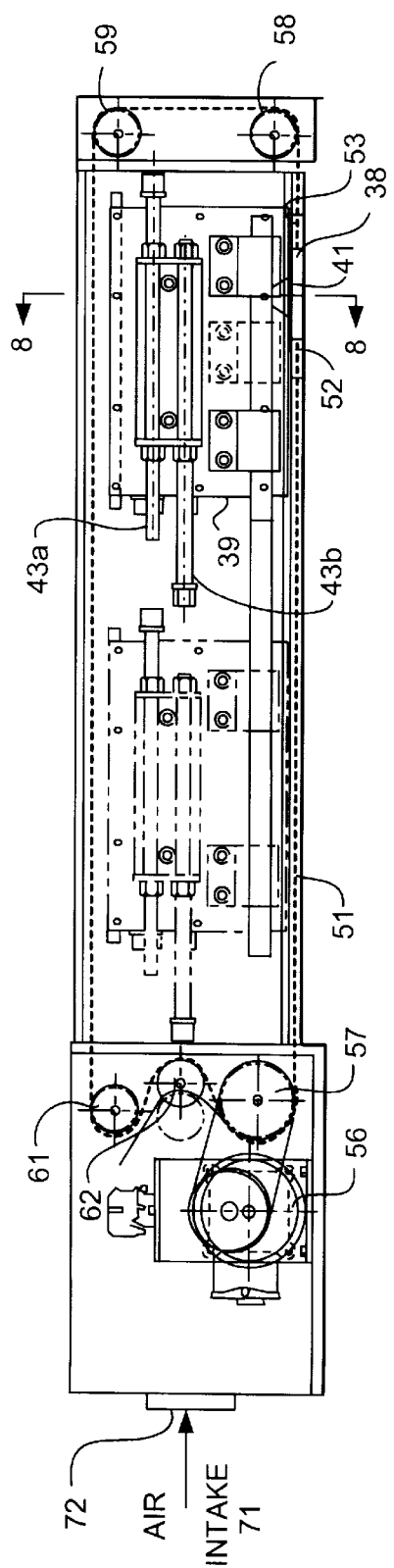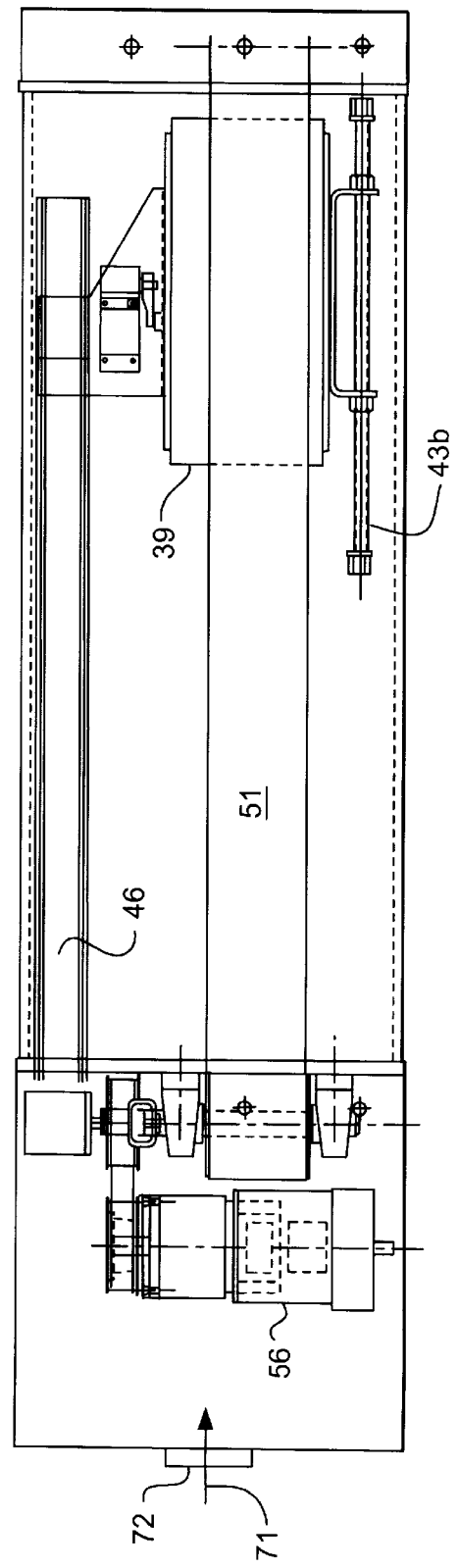

SCANNER WITH INTERIOR GAUGING HEAD AND COMBINED DUST AND DRIVE BELT

INTRODUCTION

The present invention is directed to a scanner for measuring at least one parameter of a sheet material such as the basis weight or moisture content of paper and, more specifically, to a scanner which has a combined dust and drive belt which protects an interior gauging head.

BACKGROUND OF THE INVENTION

For the measurement of the properties of a moving paper sheet which is moving in a machine direction (MD), a scanner 10, as illustrated in FIG. 1 includes a pair of gauging heads 11 and 12 which scan a sheet of material such as paper 13 in a cross direction 16 perpendicular to the machine direction 14. A gap 17 is formed by the upper and lower gauging heads through which the paper 13 passes. The gauging heads themselves are mounted on a pair of spaced upper and lower beams 19 and 21 which are supported at both ends by vertical supports 22a and 22b (the latter not being shown). As is apparent from FIG. 1 the gauging heads are external to the beams 19 and 21. Internal to the beam are guides for the gauging head and electrical and cooling lines, for example, for water and air. Each beam 19 and 21 contains a slot in which the respective gauging heads 11 and 12 are mounted for cross direction scanning. To protect the interior of the beams is a dust belt 23, as illustrated in FIG. 2, which is, for example, attached to the gauging head 11 which rides along the top of the slot to partially seal it. A separate drive belt (not shown) is also provided for actually moving or scanning the gauging head.

Because of the foregoing construction, the scanner has a large cross-section and is mechanically complicated. Since it operates in an extremely hot or moist environments in many situations, cooling water or cooled air must be supplied by a separate so called power track unit which contains tubes supplying both air, cold water and electrical wires for powering the gauging heads and receiving the measurement signals. Another important factor in the measurement procedure is that the upper and lower gauging heads must move in perfect synchronism to reduce measurement errors.

OBJECT AND SUMMARY OF THE INVENTION

It is a general object of the present invention is to provide an improved scanner for measuring at least one parameter of a sheet of moving material.

In accordance with the above object, there is provided a scanner for measuring at least one parameter of a sheet of material moving in a machine direction (MD) including gauging head means mounted for cross direction (CD) movement across the sheet, and perpendicular to the machine direction, from one edge of the sheet to the other comprising at least one tubular beam suspended over or under the sheet in the cross direction, from one said edge to the other, the beam having a continuous slot in the cross direction in proximity to such sheet to allow the gauging means to measure the parameter. Guide means are inside the tubular beam on which the gauging head means is interiorly mounted for cross direction movement within said tubular beam, such gauging head having a face exposed through the slot means to said sheet and interfacing with such sheet without physical interference for measuring a parameter of said sheet. Flexible drive belt means are substantially contained within the tubular beam and connected to the gauging head for both driving said gauging head in said cross direction and for sealing the length of the slot in the cross direction to protect the interior of said beam and the gauging head from ambient dust, dirt and air, the drive belt means including an opening at the gauging head to allow direct communication, without interference, between the gauging head face and the moving sheet.

BRIEF DESCRIPTION OF THE DRAWINGS

FIG. 3 is a top plan view, partially cut away, of a scanner incorporating the present invention.

FIG. 4 is a side elevational view of FIG. 3.

DETAILED DESCRIPTION OF THE PREFERRED EMBODIMENTS

Figure 5:
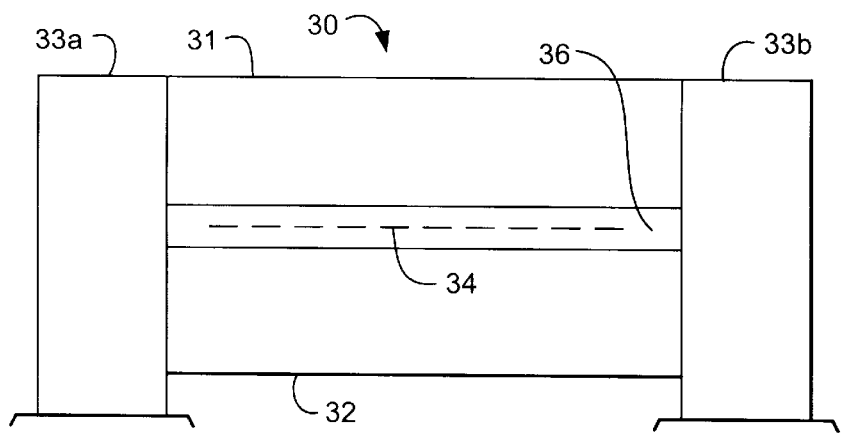
FIG. 5 is a simplified view of one embodiment of an installed scanner of FIGS. 3 and 4.

FIG. 5 illustrates a typical embodiment of scanner 30 where there are a pair of spaced upper and lower beams 31 and 32 which are supported by left and right vertical supports 33a and 33b, the vertical supports being located at the left and right edges of a moving sheet of material 34 such as paper. The width of such paper might be from 6 to 10 feet. Because of the unique construction of the beams 31 and 32 and their associated gauging heads which scan across the paper 34 in the cross direction, the gap 36, between the beams 31 and 32, is relatively small.

Figure 8:
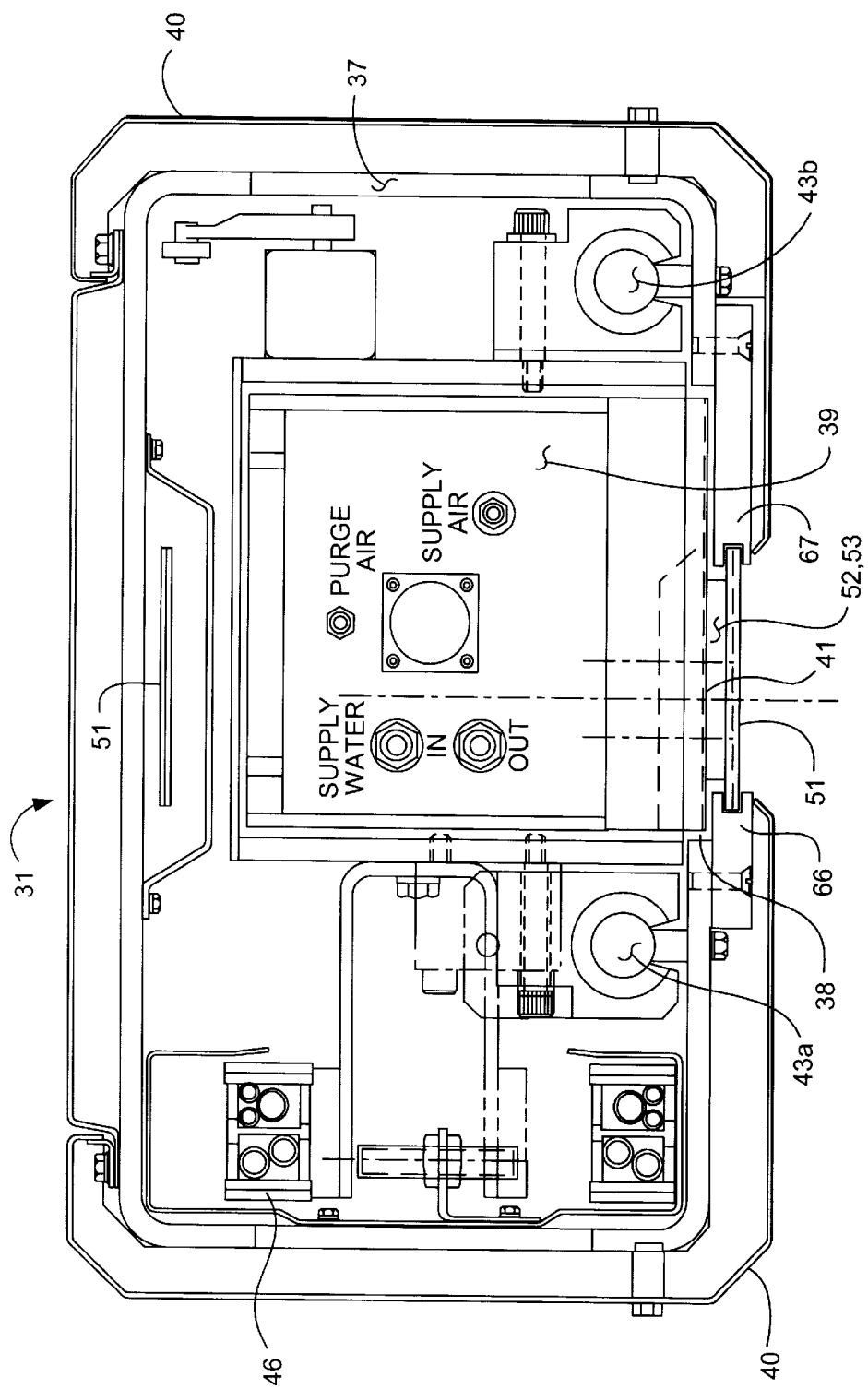
FIG. 8 is a cross-sectional view taken along the lines 8—8 of FIG. 4.

Referring to FIG. 8 where the cross-section of beam 31 is radon, its bottom portion faces the moving sheet 34. For condensation and thermal control insulated outer layer 40 is provided. A slot 38 in the bottom portion is, of course, in proximity to sheet 34 to allow an upper gauging head 39 to have its face 41 exposed through the slot to the sheet and interface with the sheet without physical interference for measuring a parameter of the sheet 34. Of course a second beam 32 would normally be on the other side of sheet 34 so that, for example, for the measurement of basis weight, a promethium source 42 contained in the upper gauging head 39 transmits radiation through the sheet and the attenuation of that radiation determines basis weight. And for moisture, of course, a pair of infrared wavelength beams are used. Gauging head 39 is mounted for slidable cross-direction movement within the beam on a pair of rods 43a, 43b.

A power track unit 46 in the form of cable with flexible links supplies the necessary electrical power, the signal line return path for measured parameters and any necessary cooling water or air to the gauging head 39. In summary, the tubular beam entirely contains and protects the gauging head 39 in its interior, and has as its only substantial opening, the slot 38.

Referring now to FIGS. 3 and 4 which are side and top views of FIG. 8 (and also referring to FIG. 8), flexible drive belt means substantially contained within the tubular beam is connected to the gauging head 39 to both drive the gauging head in the cross direction and for sealing the length of the slot in the cross direction (by covering it), to protect the interior of the beam from ambient dust, dirt and air.

FIG. 4 illustrates this flexible plastic drive belt 51 which is temperature resistant, and which is connected to gauging head 39 at a pair of leading and lagging points 52 and 53. Thus its face 41 is thereby exposed. One fastening plate 52 is better illustrated in FIG. 8. Belt 51 is driven by an appropriate motor 56 along with various pulleys 57, 58, 59, 61 and 62. Motor 56 as illustrated in FIG. 3 also drives the power track unit 46. Belt 51 is a high precision timing belt available from BRECOFLEX CO. of EATONTOWN, N.J.

In order to effectively seal the slot 38, as illustrated in FIG. 8, in one embodiment the drive belt 51 is journaled in a pair of interior recesses 66 and 67 which are parallel to the slot 38. These recesses as illustrated in FIG. 8 are preferably constructed of aluminum material or stainless steel which is located below slot 38 in the insulating material 40, but still fastened to the stainless steel tubular beam 37. Alternatively, the recesses could be a part of beam 37 or located in the interior of the beam in the same manner as shown on the exterior. Thus, the recesses provide an effective bearing for the belt 51, as well as an effective seal.

To cool the interior of the enclosed beam 31 as well as beam 32, air intake 71 is provided with an associated blower 72. The blower air inlet 71, 72 provides a positive pressure inside the beam greater than the ambient air pressure to prevent contamination inside the beam. Thus the interior of beam forms an air plenum for cooling the interior gauging heads. With this technique, water cooling of the gauging head itself, which is within the power track 46, can be eliminated in some conditions.

Figures 1, 2:
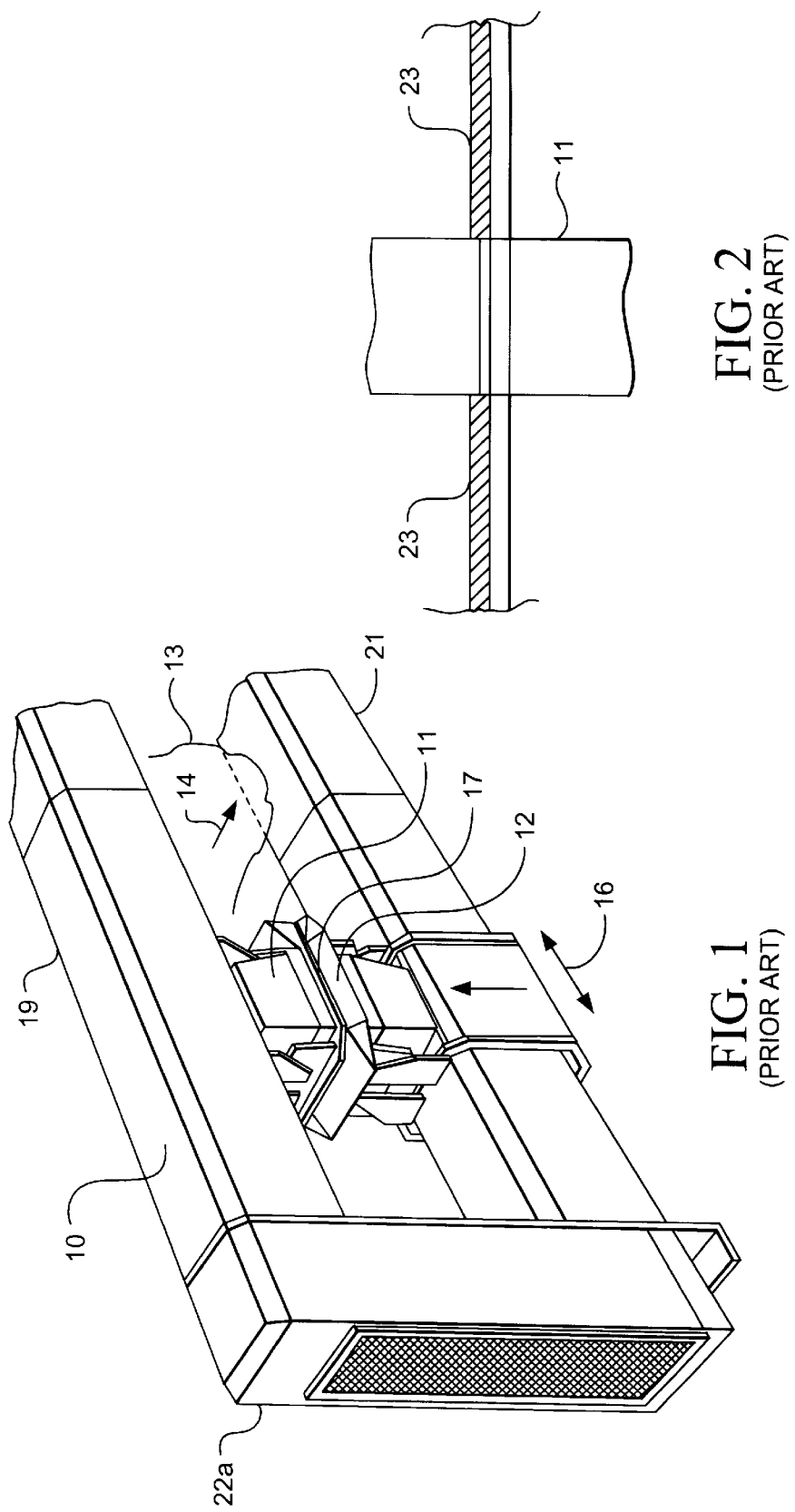
FIG. 1 is a prior art scanner.
FIG. 2 is a cross-sectional view of a portion of FIG. 1.

Another advantage is the mounting of the gauging heads much closer to their points of slidable motion (compare FIG. 1) provides for greater accuracy and synchronism of motion. The compact size illustrated in FIG. 5 is also beneficial from both an installation standpoint and from a measurement standpoint.

Figure 6:
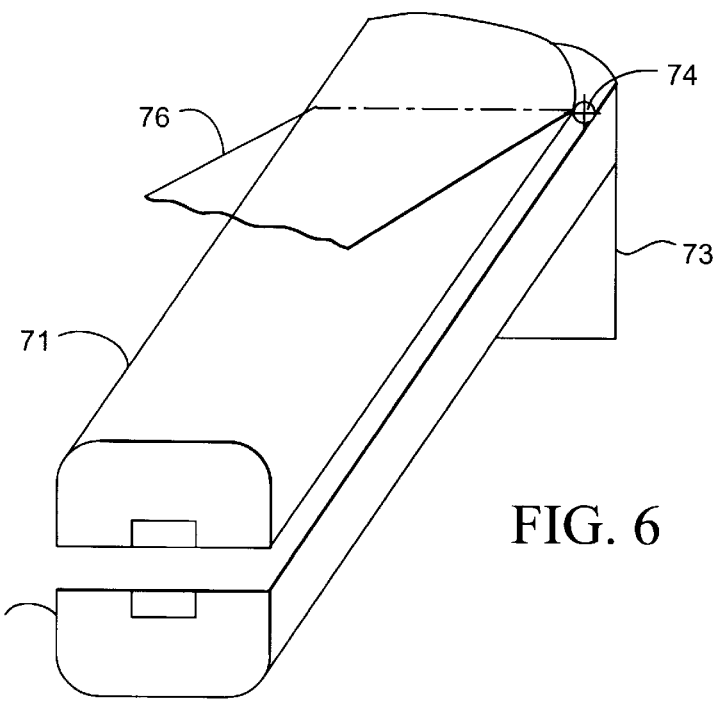
FIG. 6 is a perspective view of an alternative embodiment.
Figure 7:
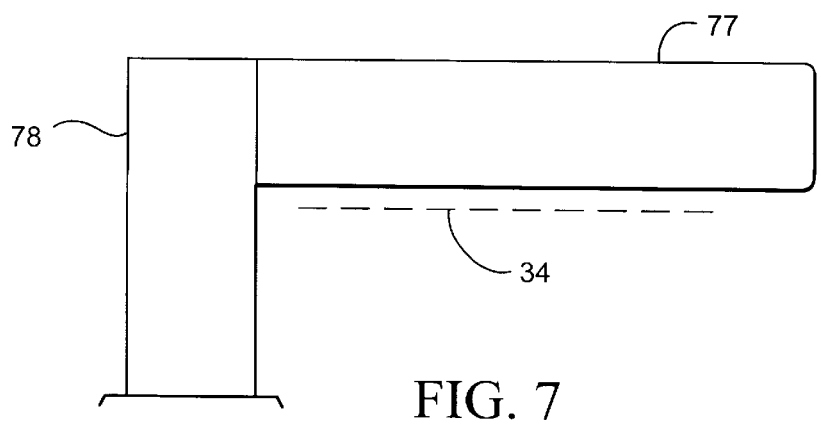
FIG. 7 is a side view of an alternative embodiment.

Alternative beam arrangements are possible, for example, as illustrated in FIG. 6, where there are a pair of cantilevered beams 71, 72, cantilevered from the vertical support 73, which is useful for some applications. Here a pivot point 74 allows either one or both beams to be pivoted as indicated by the dashed outline 76 for repair and/or installation and/or receiving a new sheet of paper. Finally, FIG. 7 illustrates another embodiment where a single beam 77 is cantilevered from a vertical support 78 over the paper 74 or the moving sheet material 34.

Thus, an improved scanner has been provided.

What is claimed is:

1. A scanner for measuring at least one parameter of a sheet of material moving in a machine direction (MD) including gauging head means mounted for cross direction (CD) movement across said sheet, and perpendicular to said machine direction, from one edge of the sheet to the other comprising:

at least one tubular beam suspended over or under said sheet in said cross direction, from one said edge to the other, said beam having a continuous slot in said cross direction in proximity to such sheet to allow said gauging means to measure said parameter;

guide means inside said tubular beam on which said gauging head means is interiorly mounted for cross direction movement within said tubular beam, such gauging head having a face exposed through said slot means to said sheet and interfacing with such sheet without physical interference for measuring a parameter of said sheet;

flexible drive belt means substantially contained within said tubular beam and connected to said gauging head for both driving said gauging head in said cross direction and for sealing the length of said slot in said cross direction to protect the interior of said beam and said gauging head from ambient dust, dirt and air, said drive belt means including an opening at said gauging head to allow direct communication, without interference, between said gauging head face and said moving sheet.

2. A scanner as in claim 1 where said tubular beam is the sole structural support for said gauging head across said moving sheet.

3. A scanner as in claim 1 including means for mounting at least one tubular beam cantilevered above or below said moving sheet.

4. A scanner as in claim 1 where a pair of beams are suspended both over and under said sheet and supported by vertical supports at both edges of the sheet.

5. A scanner as in claim 1 where said slot has a predetermined width and includes a pair of interior recesses parallel to said slot for accommodating said belt and for providing a bearing for said belt for its movement and for providing an effective seal.

6. A scanner as in claim 1 including air inlet means for cooling the interior of said beam and providing a positive pressure inside said beam greater than the ambient outside air pressure.

7. A scanner as in claim 1 where said sheet of material is paper and said parameters include basis weight and moisture.

8. A scanner as in claim 1 where said beam includes a layer of insulating material.

* * * * *